US012623064B2

(12) United States Patent
Lee et al.

(10) Patent No.: US 12,623,064 B2
(45) Date of Patent: May 12, 2026

(54) STEREOTACTIC GUIDANCE DEVICE

(71) Applicants: MYO SEONG, Anyang-si (KR);
**SAMSUNG LIFE PUBLIC
WELFARE FOUNDATION**, Seoul
(KR)

(72) Inventors: Boo Rak Lee, Gimpo-si (KR); **Ji Won
Seong, Incheon (KR); Duk Lyul Na**,
Seoul (KR); Seung Hoon Lee, Seoul
(KR); Jeong Min Lee, Seoul (KR);
Woo Ram Jung, Seoul (KR); **Kap Soo
Kim, Seoul (KR); Nak Soon Park**,
Wonju-si (KR)

(73) Assignees: MYO SEONG, Anyang-si (KR);
**SAMSUNG LIFE PUBLIC
WELFARE FOUNDATION**, Seoul
(KR)

( * ) Notice: Subject to any disclaimer, the term of this
patent is extended or adjusted under 35
U.S.C. 154(b) by 932 days.

(21) Appl. No.: 17/802,106

(22) PCT Filed: Dec. 21, 2020

(86) PCT No.: PCT/KR2020/018762
§ 371 (c)(1),
(2) Date: Aug. 24, 2022

(87) PCT Pub. No.: WO2021/172725
PCT Pub. Date: Sep. 2, 2021

(65) Prior Publication Data
US 2023/0081294 A1 Mar. 16, 2023

(30) Foreign Application Priority Data

Feb. 24, 2020 (KR) ......................... 10-2020-0022446

(51) Int. Cl.
| | |
|---|---|
| *A61M 39/02* | (2006.01) |
| *A61B 90/10* | (2016.01) |
| *A61B 90/11* | (2016.01) |

(52) U.S. Cl.
CPC ......... *A61M 39/0247* (2013.01); *A61B 90/11*
(2016.02); *A61B 2090/103* (2016.02); *A61M
2039/025* (2013.01)

(58) Field of Classification Search
CPC ............... A61M 39/0247; A61B 90/11; A61B
2090/103; A61B 17/3403
See application file for complete search history.

(56) References Cited

U.S. PATENT DOCUMENTS

| | | | |
|---|---|---|---|
| 6,579,267 B2 | 6/2003 | Lynch et al. | |
| 6,902,569 B2 * | 6/2005 | Parmer | .................. A61B 90/11 |
| | | | 606/108 |

(Continued)

FOREIGN PATENT DOCUMENTS

| | | |
|---|---|---|
| JP | 2019-018342 A | 2/2019 |
| JP | 2009-544406 A | 12/2019 |

(Continued)

*Primary Examiner* — Bradley J Osinski
(74) *Attorney, Agent, or Firm* — Han's Law Office

(57) ABSTRACT

Disclosed is a stereotactic guidance device comprising a
guide handle coupled inside the driving part, and configured
to accommodate a guide tube unit, adjusting the guide tube
unit to be positioned toward a target point, and guiding the
guide tube unit so that the guide tube unit is provided inside
the driving part; a probe accommodating part provided at the
guide handle and accommodating a navigation probe; a tube
connecting part connected to the guide handle, provided as
at least a pair of members to be assembled and disassembled,
having one end portion inserted into the guide handle and the
other end portion mounted at an upper portion of the guide
handle, and guiding the guide tube unit so that the guide tube (Continued)

unit is inserted into and mounted in the driving part; and a guide wire provided in the guide handle and the guide tube unit.

8 Claims, 16 Drawing Sheets

(56) References Cited

U.S. PATENT DOCUMENTS

| | | | |
|---|---|---|---|
| 7,896,889 | B2 | 3/2011 | Mazzocchi et al. |
| 9,669,198 | B2 | 6/2017 | Broaddus et al. |
| 2005/0070920 | A1 | 3/2005 | Solar et al. |
| 2005/0131386 | A1 | 6/2005 | Freeman et al. |
| 2005/0245896 | A1 | 11/2005 | Kucharczyk et al. |

FOREIGN PATENT DOCUMENTS

| | | |
|---|---|---|
| KR | 10-2010-0103287 A | 9/2010 |
| KR | 10-2020-0086874 A | 7/2020 |

* cited by examiner

[FIG. 2]
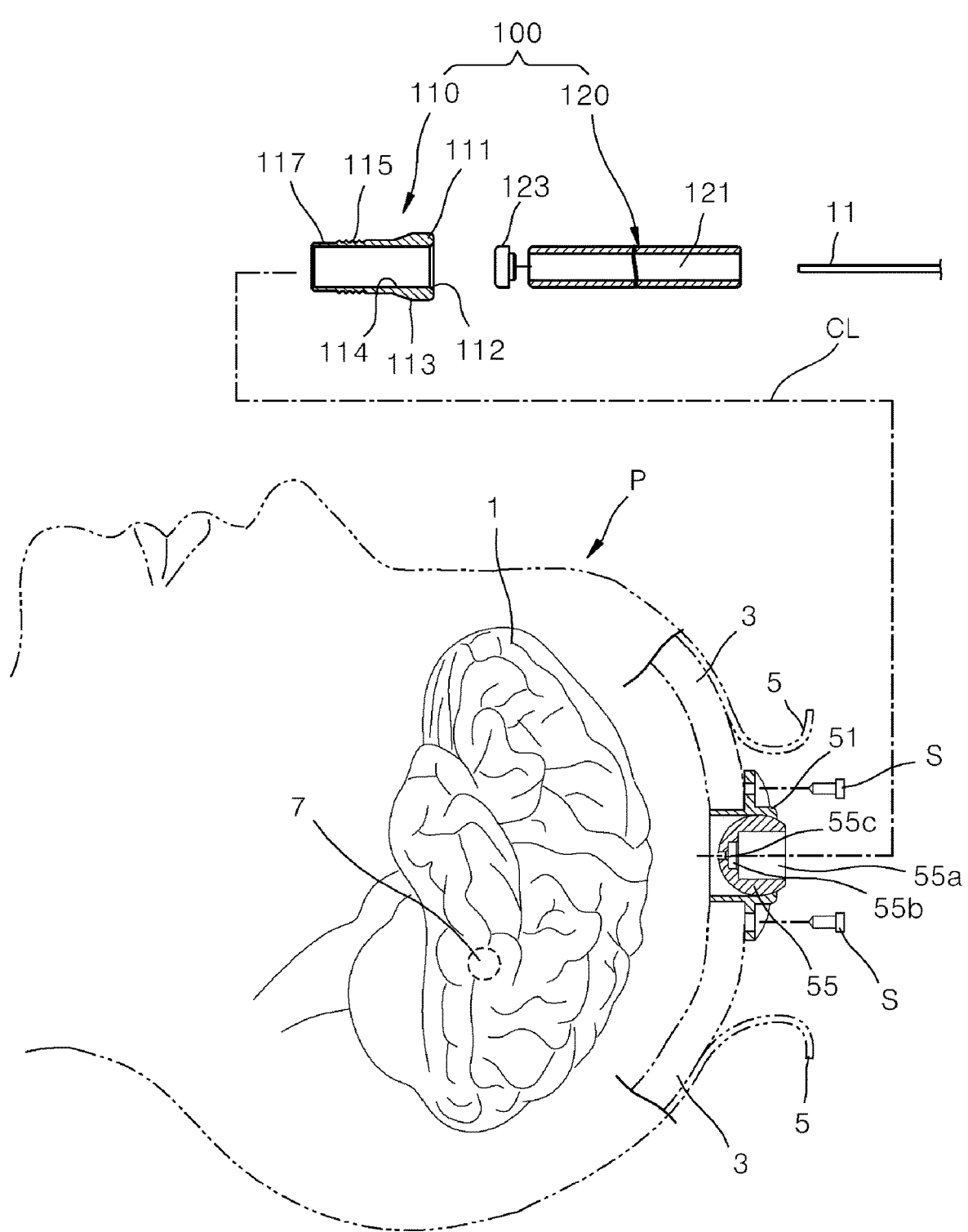

[FIG. 3A]
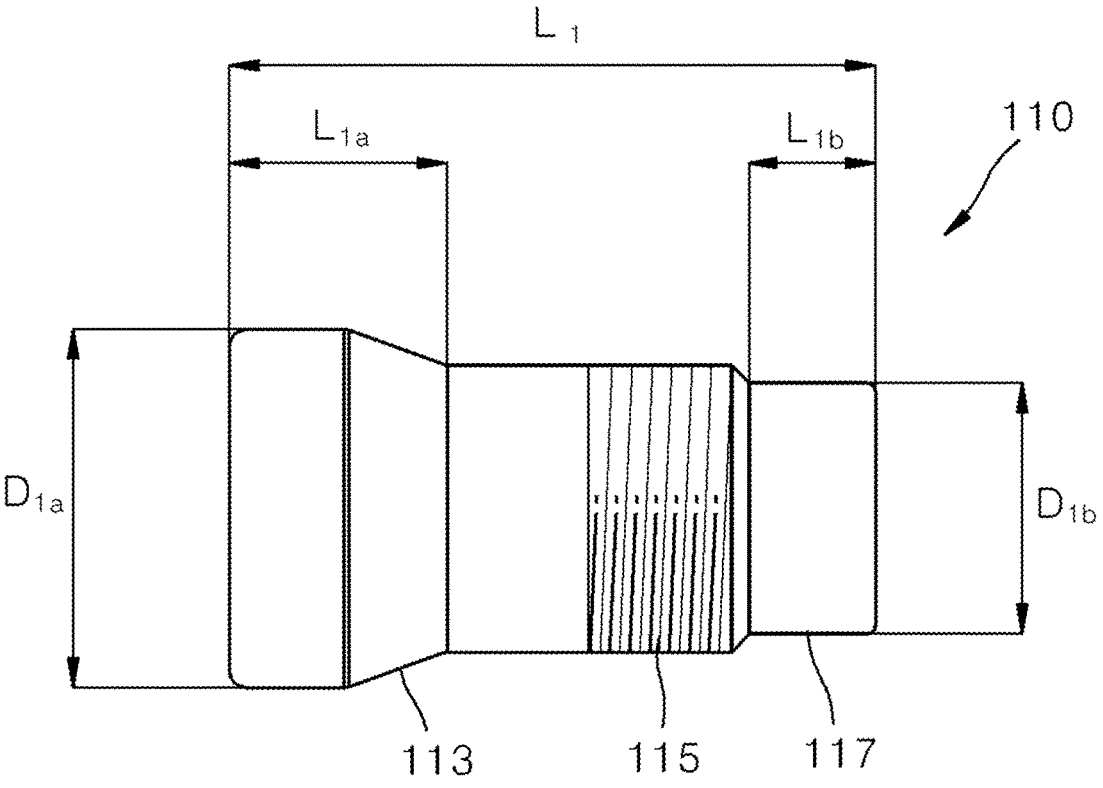
[FIG. 3B]
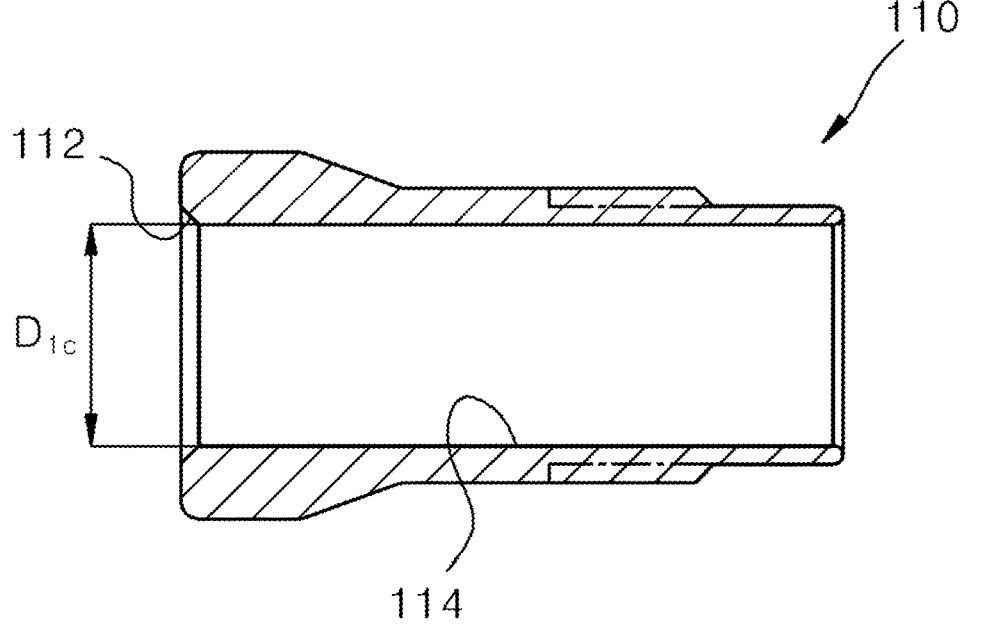

[FIG. 4]
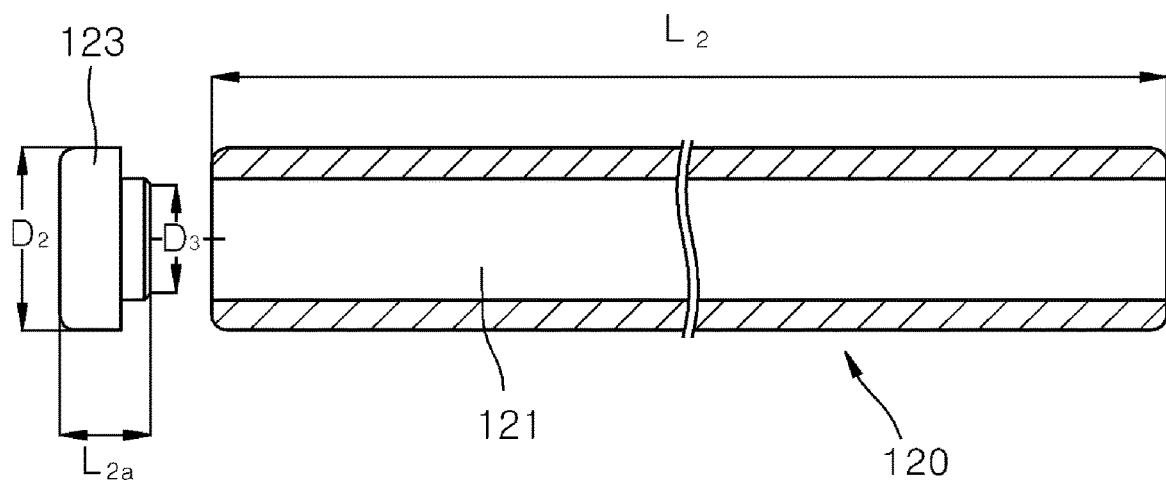

[FIG. 5A]
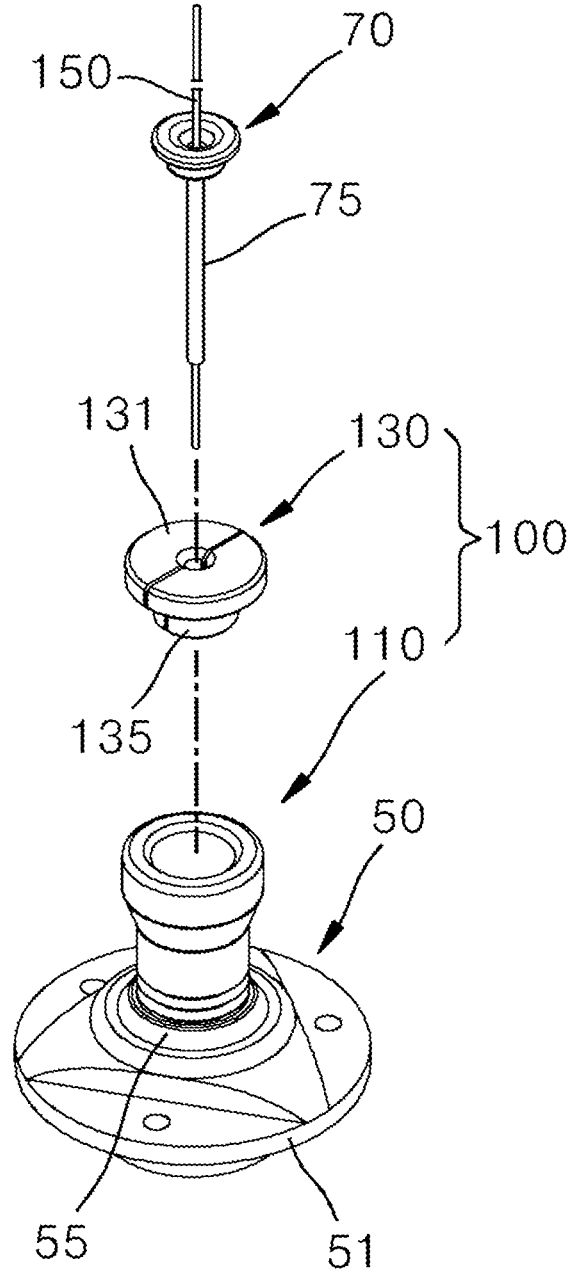

[FIG. 5B]
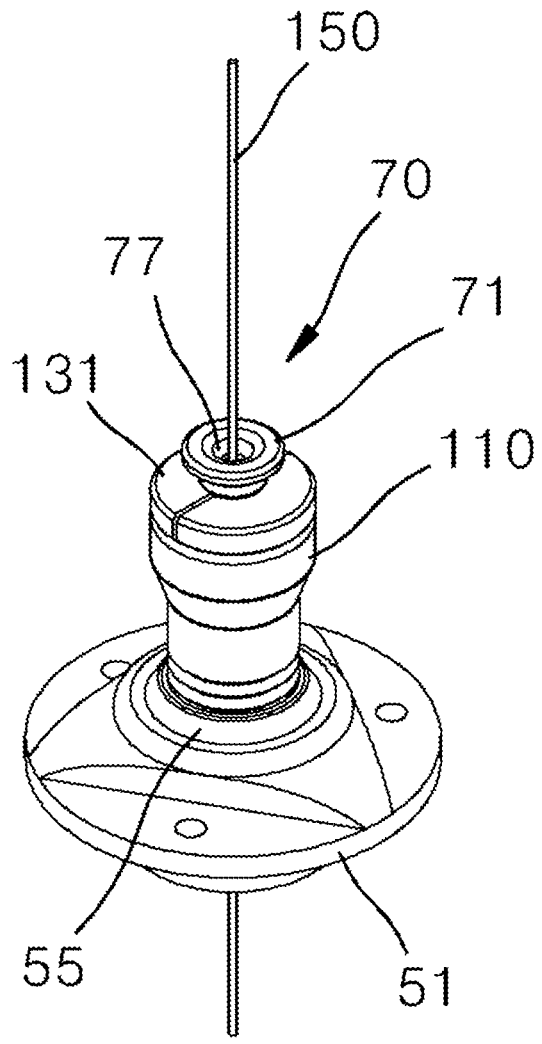

[FIG. 5C]
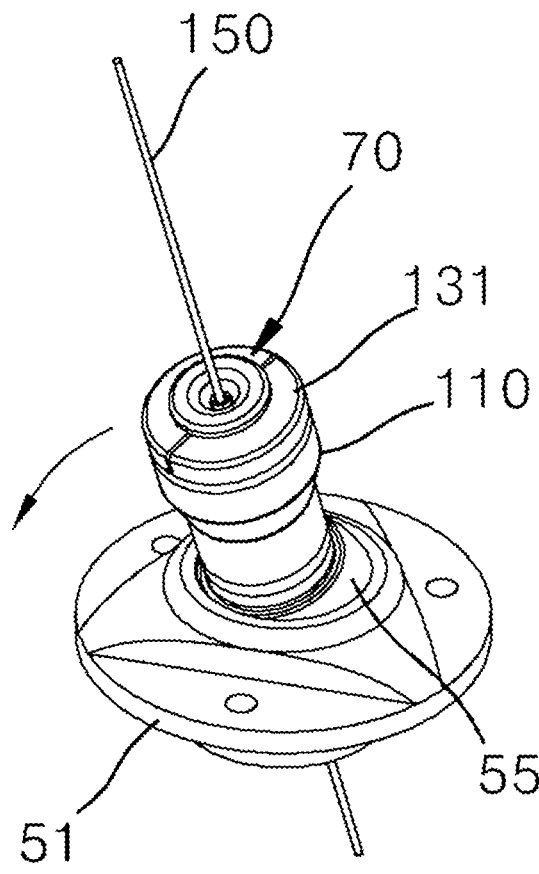

[FIG. 5D]
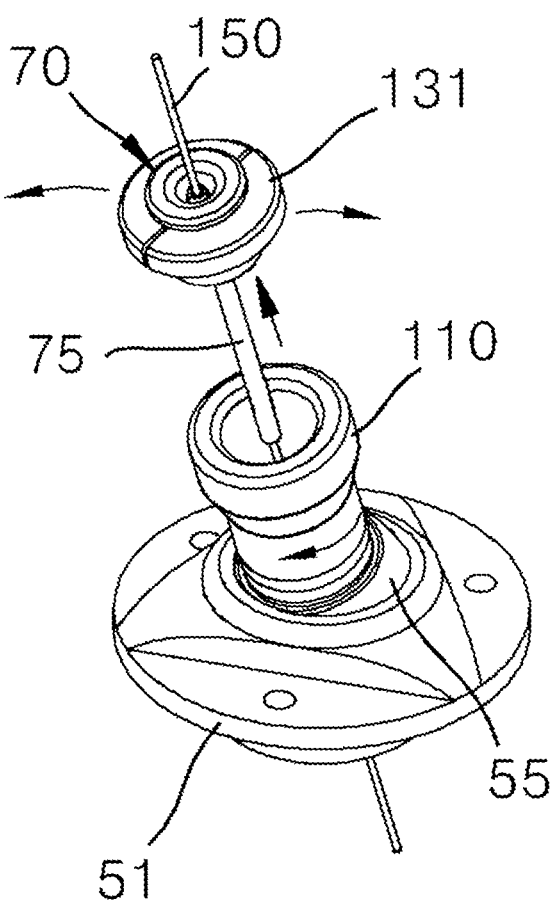

[FIG. 5E]
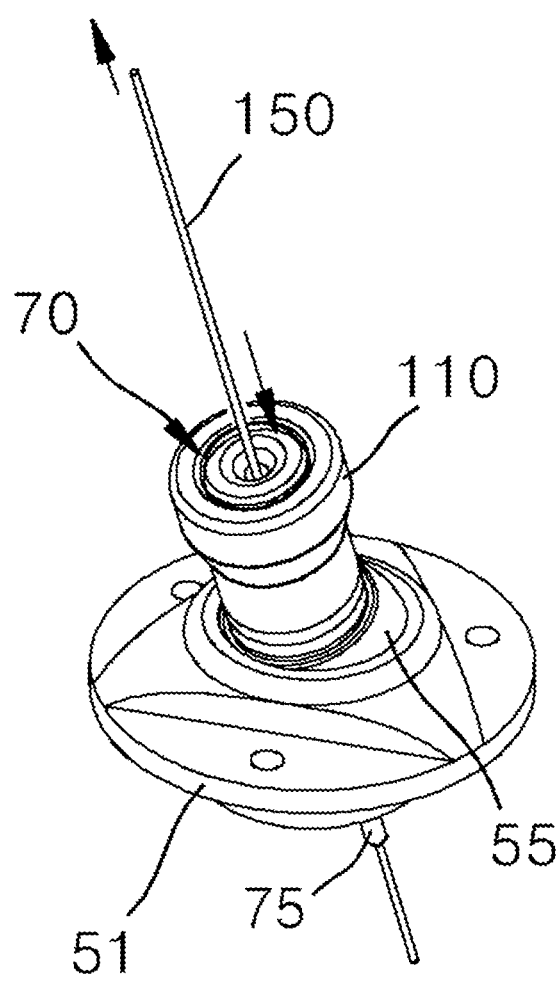

[FIG. 6]
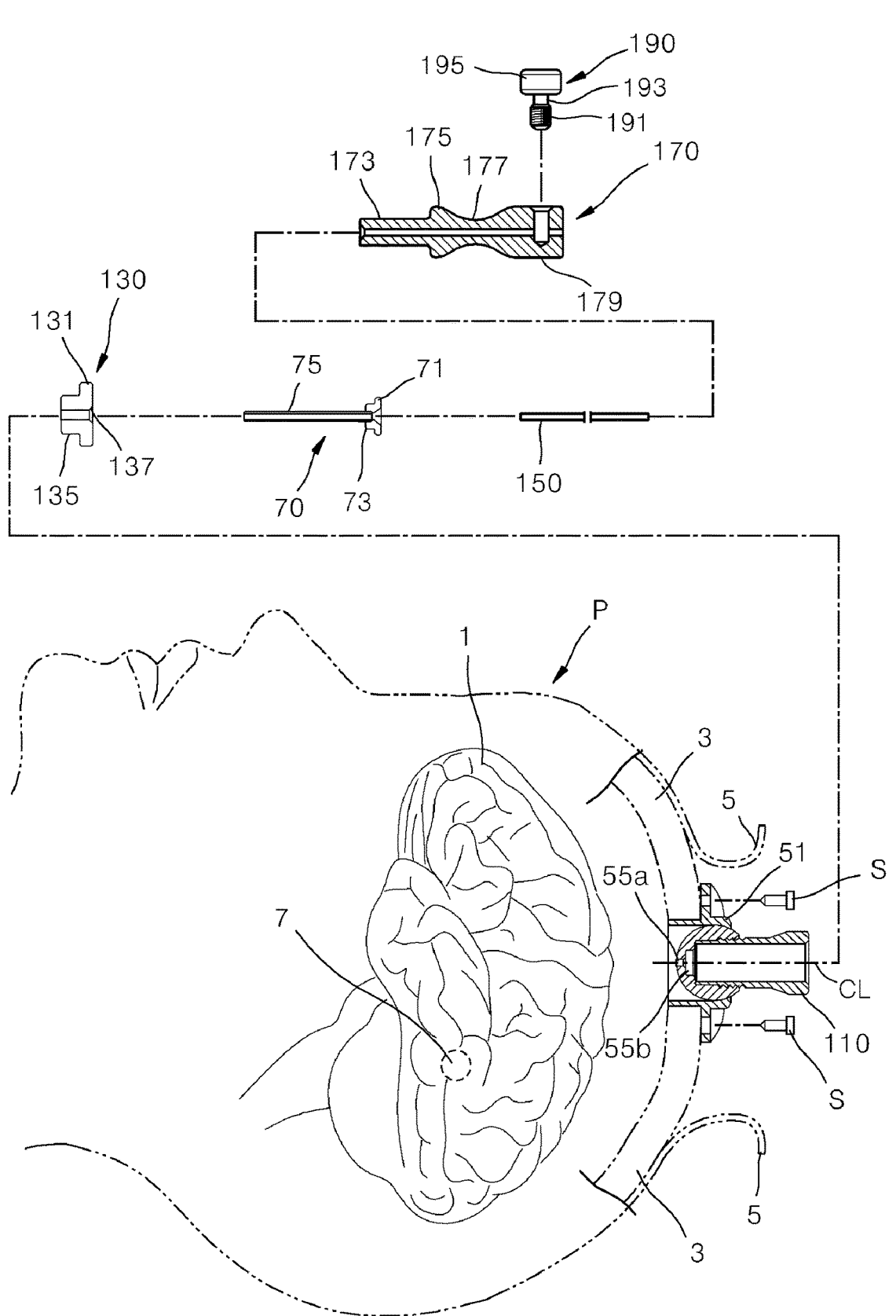

[FIG. 8A]
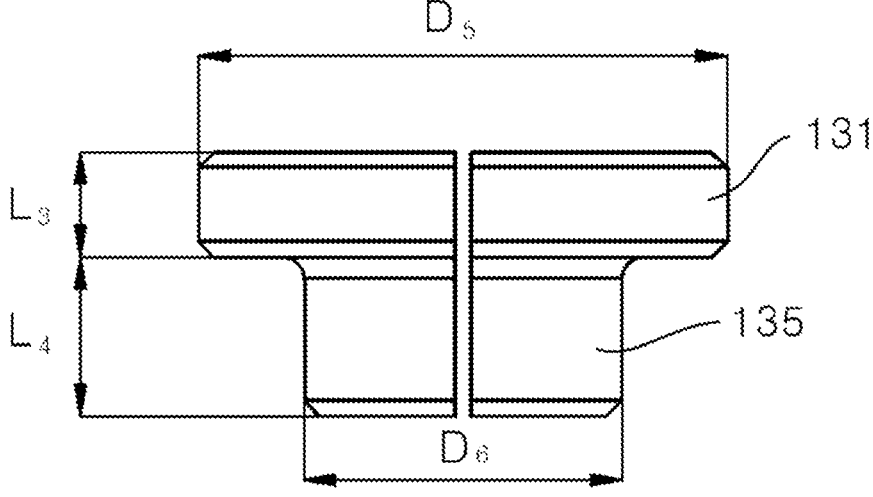
[FIG. 8B]
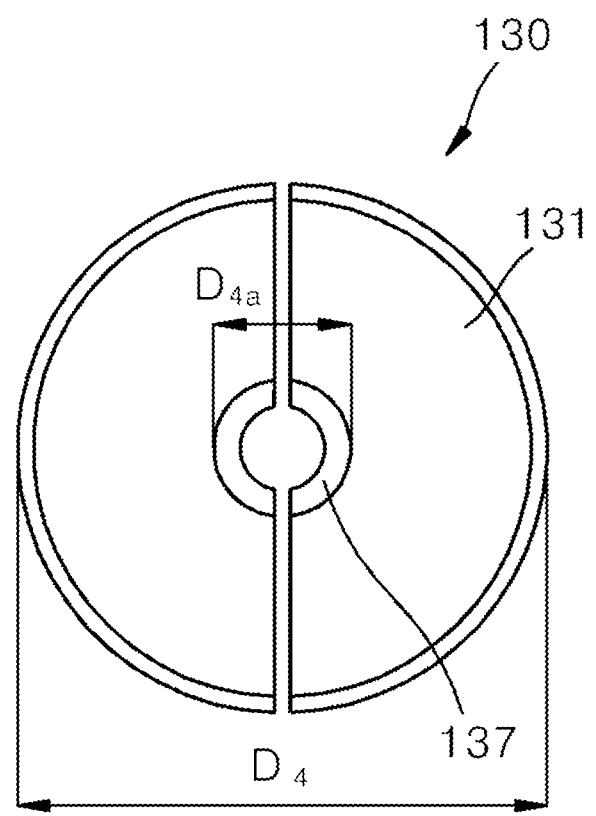

[FIG. 8C]
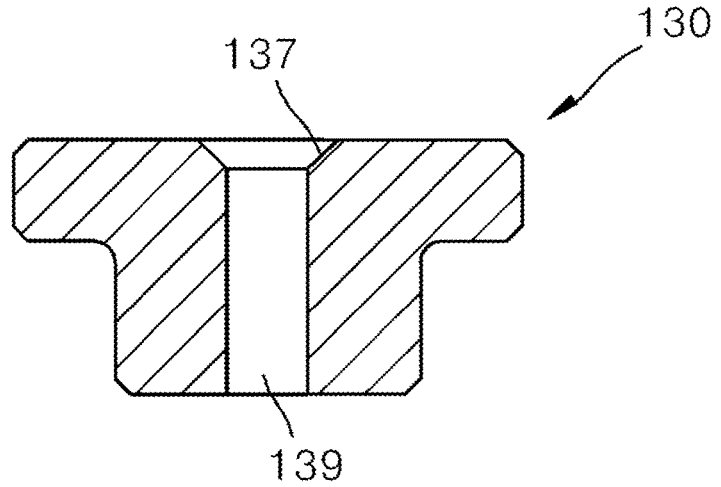
[FIG. 9]
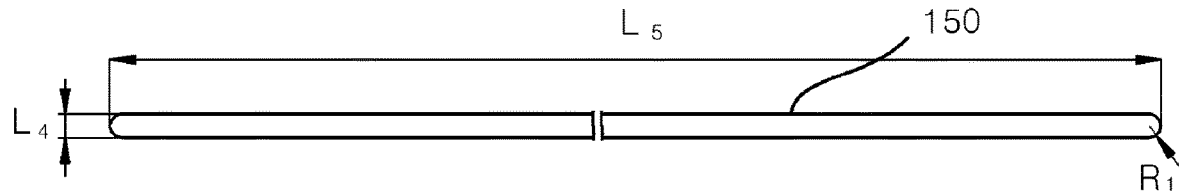

[FIG. 10]
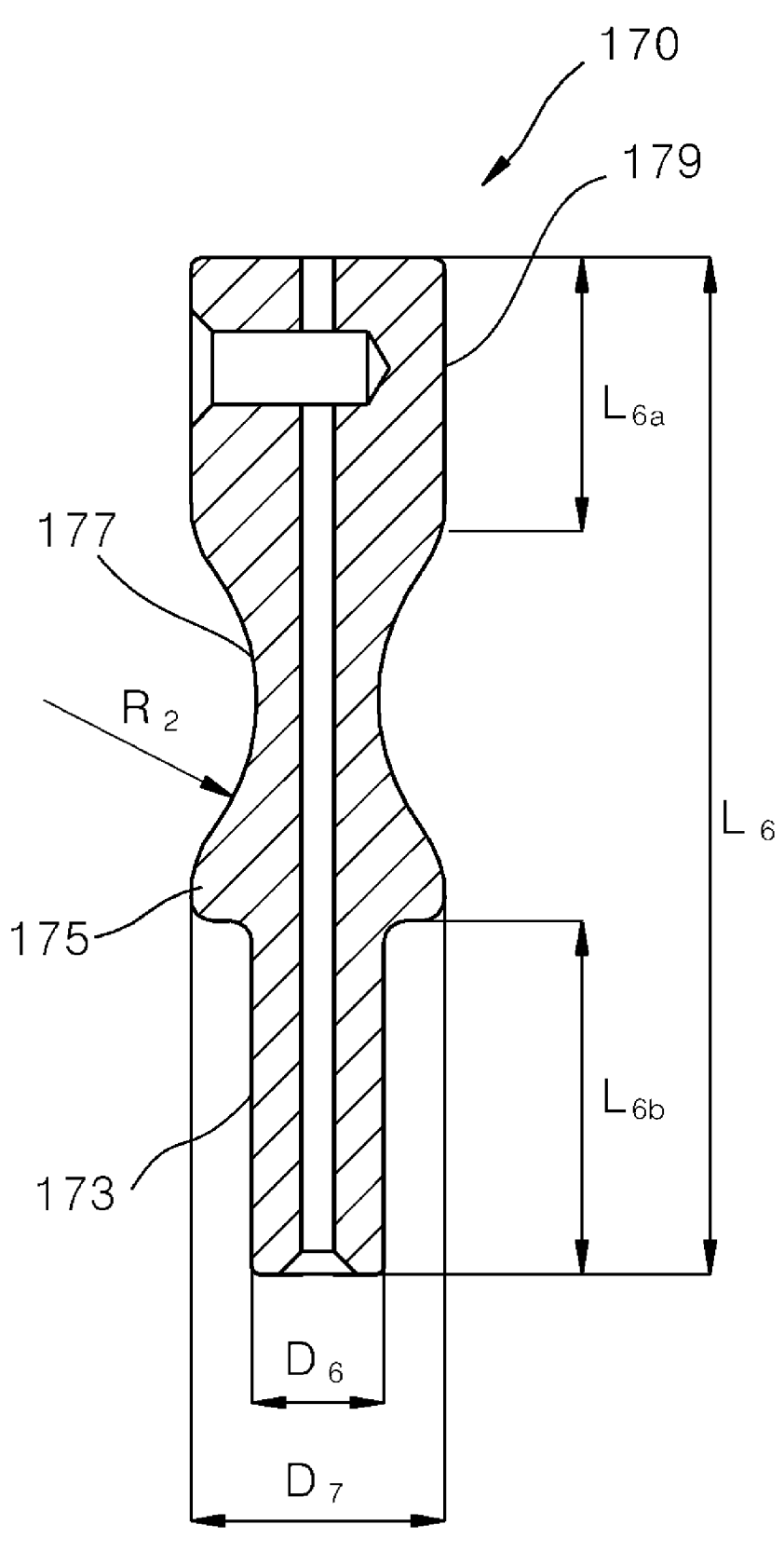

[FIG. 11]
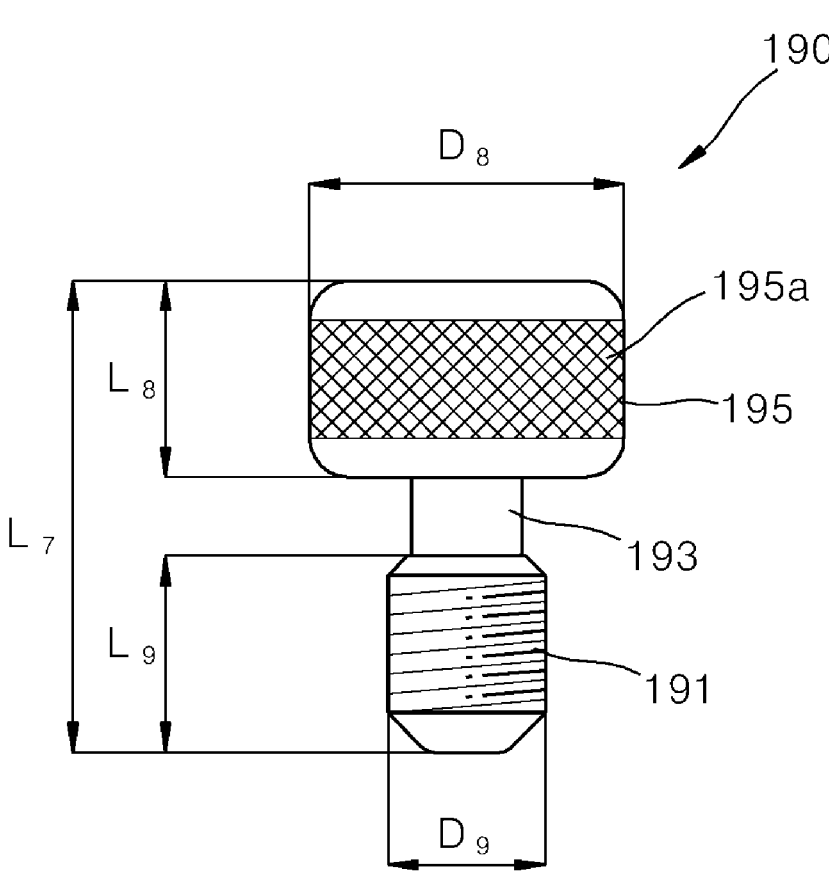

[FIG. 12]
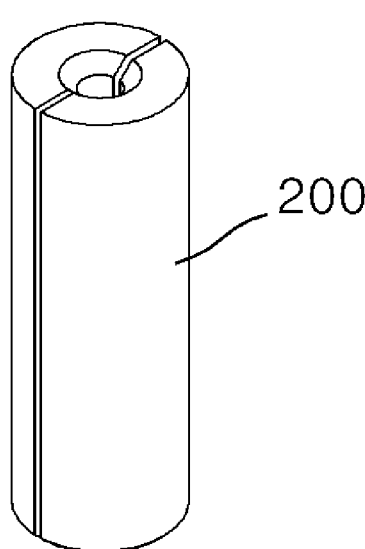

STEREOTACTIC GUIDANCE DEVICE

FIELD OF INVENTION

The present invention relates to a stereotactic guidance device, and particularly to, a stereotactic guidance device with improved precision, accuracy, and ease of use for guiding a drug injection device for repeatedly administering a drug so that the drug injection device is mounted at a target point within the skull of a patient.

BACKGROUND OF THE INVENTION

Recently, diseases that lower quality of life such as diabetic, psychiatric, and cancer require continuous and repeated drug administration in order to control blood sugar rise or reduce pain. However, in the case of patients with gastrointestinal cancer such as gastric cancer, the traditional oral administration method may have difficulties in drug administration itself, and may cause side effects due to systemic circulation of drugs. On the other hand, since a method of directly administering drugs to the spinal cord, which is a nerve route, exhibits drug effects 300 times greater than oral administration and 100 times greater than intravenous administration, hospitalization for administration of drugs such as insulin and painkillers is unnecessary, and thus, it is possible to reduce the number of days of stay for pain treatment, thereby reducing social and economic costs.

Accordingly, a drug injection device for repeated drug administration is designed to be mounted on a part of the body such as the patient's abdomen and brain in order to repeatedly administer fluids such as insulin, dementia treatment agents, and subcutaneously administered drugs for brain diseases.

In this regard, in the case of patients with brain tumors, brain diseases, and dementia, in drug administration, it is necessary to effectively deliver a drug into the brain for remedial results. Accordingly, in preferentially considering the drug delivery efficiency, the best method is to directly administer the drug into the brain parenchyma after incising a surgical site to form a bur hole and mounting the drug injection device in the bur hole. On the other hand, the biggest barrier to direct administration using the drug injection device is a route of administration. In the case of a drug that targets the brain, there is a difficulty in that the drug should pass through the blood-brain barrier (BBB). Further, in the case of repeated administration, it is not easy to implant the drug injection device at the same target location again, and in a case where it is implanted at a slightly different point, side effects such as post-operative inflammation may occur, which increases the cost of surgery and causes side effects.

Accordingly, the drug injection device needs to be mounted to enable repeated administration. Here, in making the drug reach the target point using the drug injection device, the drug injection device should be connected and mounted while avoiding the surrounding structures that control important brain functions. In addition, a stereotactic guidance device is needed for guiding direction change of a guide tube of the drug injection device through a bur hole formed by making a hole in the skull and to accurately aim the guide tube toward a lesion that is the target point.

In the related art, so-called "frameless stereotaxy" that is mounted in or around a bur hole to provide surgical guidance to a neurosurgeon and assist in planning or performing surgery has been proposed.

However, this technique has a complicated structure and takes a lot of time to mount the device. Further, this technique has a limitation in that since the bur hole of the skull has a limited diameter, the size and position of a target region in the brain parenchyma that can be accessed through the bur hole are also limited. That is, since the drug injection device is mounted so that a central axis is set from a position where the drug injection device is initially mounted on the skull to the target point, in a case where the target point is moved or the drug needs to be injected at a different target point, there is a limitation in that the skull should be punctured at another position.

SUMMARY OF THE INVENTION

To solve the above-mentioned problems, an object of the present invention is to provide a stereotactic guidance device capable of guiding a guide tube of a drug injection device to be positioned toward a target point in the brain parenchyma of a patient with brain-related diseases and diseases, precisely and accurately positioning the guide tube close to the target point, and enabling direction change with respect to a central axis.

Further, another object of the present invention is to provide a stereotactic guidance device capable of being easily handled by an operator in mounting and removal.

According to an aspect of the present invention, there is provided a stereotactic guidance device that rotates a driving part of a drug injection device in order to find a target point in a patient's skull and is detachably provided so that a guide tube unit can be provided in the driving part, including: a guide handle that is coupled inside the driving part, and is configured to accommodate the guide tube unit, adjust the guide tube unit to be positioned toward the target point, and guide the guide tube unit so that the guide tube unit is provided inside the driving part; a probe accommodating part that is provided at the guide handle and accommodates a navigation probe that finds a trajectory for the target point; a tube connecting part that is connected to the guide handle, is provided as at least a pair of members to be assembled and disassembled, has one end portion inserted into the guide handle and the other end portion mounted at an upper portion of the guide handle, and guides the guide tube unit so that the guide tube unit is inserted into and mounted in the driving part; and a guide wire that is provided in the guide handle and the guide tube unit, and guides and adjusts a direction toward the target point.

The guide handle may have a coupling hole that is formed in a hollow shape so that at least one of the probe accommodating part, the navigation probe, the guide wire, and the guide tube unit is inserted therein, and may include an insertion part that is inserted in the driving part; a coupling part that is extended from the insertion part and is coupled to the driving part; a handling part that is formed to be tapered in the coupling part and is located outside the driving part to perform handling during a procedure; and an insertion guide part that is formed to be rounded inside the handling part, is located at an end portion of the coupling hole, and guides insertion of the tube connecting part in a direction of the coupling hole when the tube connecting part is inserted therein.

A probe insertion hole may be formed inside the probe accommodating part, and the probe accommodating part may include a central axis aligning part that has at least one side that is inserted into the driving part and is flatly blocked, and is configured to find the nearest target point by aligning the central axis without a direction error when the driving part rotates.

The tube connecting part may be formed with a guide hole at the central portion thereof, in which at least one of the guide wire and the guide tube is inserted and directed to the target point, and serves as a double guide together with the guide handle, and may include a first connecting part that is mounted on the guide handle; and a second connecting part that is extended from the first connecting part, has a smaller diameter, and is inserted into the guide handle.

The guide wire may be formed in a round shape at a tip thereof inserted into brain parenchyma.

The stereotactic guidance device may include a wire handling part that performs handling without shaking during insertion into the target point and the procedure, and is formed with a hole in which the guide wire is inserted at a central portion thereof.

The wire handling part may include: a fixing part that is fixedly accommodated in the guide handle; a grip part that is connected to the fixing part and is formed with a gripping groove to be gripped in handling the guide wire on at least one side thereof; a mounting part that is connected to the grip part and is mounted on the guide handle; and a fastening accommodation part that is formed with a fastening groove on at least one side thereof to enable fixed coupling between the guide wire and the wire handling part.

The wire handling part may further include: a fastening part that is provided to be fit-coupled in the fastening accommodation part, and the fastening part may include: a head part having a concave and convex pattern formed on the outside thereof to prevent slipping in rotational handling of the fastening part; a body part that is fastened to the fastening accommodation part, and provides the fixed coupling between the guide wire and the wire handling part; and a neck part that is positioned between the head part and the body part, and is configured to provide height adjustment to facilitate fastening and separation of the head part and the body part.

In the stereotactic guidance device according to the present invention, in a case where the target point is moved from the position where the drug injection device is first mounted or the drug needs to be repeatedly injected to another target point, it is possible to accurately find the new target point by adjusting the insertion angle of the guide tube.

Further, since the stereotactic guidance device according to the present invention includes the probe accommodating part with a closed end, it is possible to perform guidance for the nearest target point by alignment of the central axis without a direction error when the driving part rotates.

In addition, since the stereotactic guidance device according to the present invention includes the guide wire with a rounded end, it is possible to reduce damage of the brain parenchyma when inserted into the brain parenchyma, and to perform the direction guidance and adjustment toward the target point using the guide tube unit.

BRIEF DESCRIPTION OF DRAWINGS

FIG. 2 is an enlarged view of FIG. 1, which shows a state where the stereotactic guidance device is positioned between the drug injection device mounted on the patient's skull and the navigation device and performs the relay and guidance.

FIGS. 3A and 3B are a side view and a side sectional view, respectively, showing a configuration of a guide handle in the stereotactic guidance device shown in FIG. 2.

FIG. 4 shows a side sectional view showing a configuration of a probe accommodating part in the stereotactic guidance device shown in FIG. 2, and a side view showing a central axis aligning part.

FIGS. 5A to 5E show a perspective view showing states where the stereotactic guidance device according to the embodiment of the present invention is mounted.

FIG. 6 is an exploded sectional view showing a state where a guide tube unit in the drug injection device mounted on the patient's skull is guided using the stereotactic guidance device according to the embodiment of the present invention.

FIGS. 8A to 8C are a side view, a plan view, and a side sectional view showing a configuration of a tube connecting part in the stereotactic guidance device shown in FIGS. 5A to 5D and FIG. 6.

FIG. 9 is a side view showing a configuration of a guide wire in the stereotactic guidance device shown in FIGS. 5A to 5D and FIG. 6.

FIG. 10 is a side view showing a configuration of a wire handling part coupled to the guide wire shown in FIG. 9.

FIG. 11 is a side view showing a configuration of a fastening part fastened to the wire handling part shown in FIG. 9.

FIG. 12 is a perspective view showing a configuration of a tube connecting part in a stereotactic guidance device according to another embodiment of the present invention.

DETAILED DESCRIPTION OF THE INVENTION

Hereinafter, a stereotactic guidance device according to an embodiment of the present invention will be described in detail with reference to the accompanying drawings. Here, the accompanying drawings may be shown by exaggerating or simplifying a part of a configuration for convenience and clarity of explanation and understanding of the configuration and operation of the invention, and each component may not exactly match an actual size.

Figure 1:
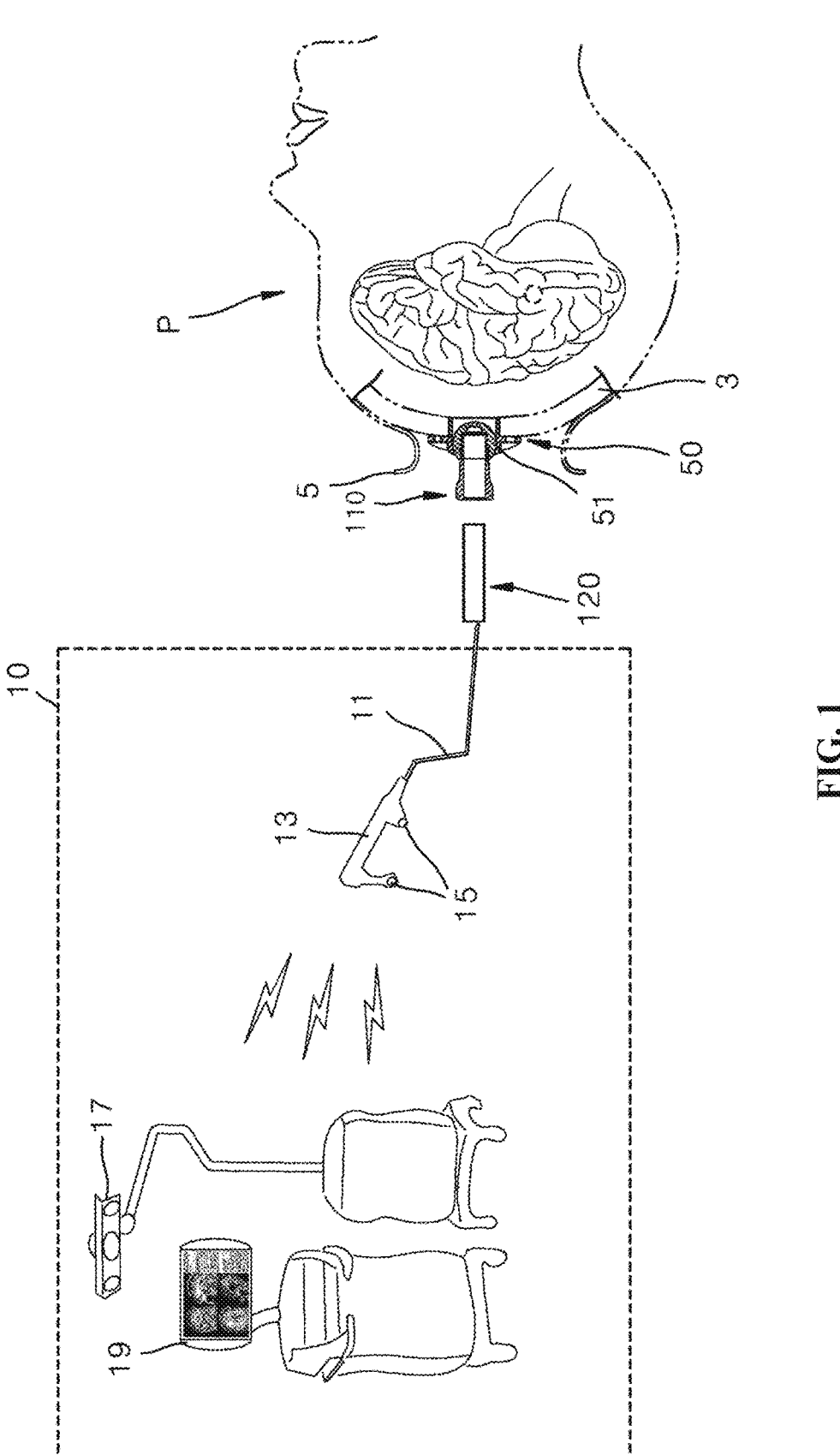
FIG. 1 is a diagram showing a state where in a stereotactic guidance device according to an embodiment of the present invention, which relays and guides insertion of a surgical navigation device into a drug injection device, the navigation device finds a position of a target point in the skull of a patient.

FIG. 1 is a diagram showing a state where in a stereotactic guidance device according to an embodiment of the present invention, which relays and guides insertion of a surgical navigation device 10 into a drug injection device 50, the navigation device 10 finds a position of a target point 7 in the skull of a patient P.

Referring to FIG. 1, the navigation device 10 may be used when performing an operation on the patient P related to a brain disease that needs drug injection into the patient's brain. Here, the brain disease may be related to, for example, a brain tumor, an intracerebral hematoma, a deep tissue biopsy, a stroke, Alzheimer's which is a dementia disease, a mental disease such as Parkinson's, depression, or schizophrenia.

The drug injection device 50 is implanted by making a bur hole on the skull 3 of the patient P, and includes a main body 51, a driving part 55, and a guide tube unit 70. The main body 51 is implanted in the skull, in which an upper end portion thereof is positioned between the scalp 5 and the skull 3, and a lower end portion thereof is inserted into the skull 3. The driving part 55 having a spherical shape with an open upper portion is inserted into the main body 51, and may perform direction change toward a target point 7 that is a lesion in the brain parenchyma. The guide tube unit 70 may be configured so that a needle for injecting brain disease-related drugs is accommodated therein. For example, a trocar needle, an injection needle, a needle for examination, or the like may be accommodated therein. However, the present invention is not limited thereto, and various instruments and equipment, other than the trocar needle or the like, for example, a navigation probe, a stimulation lead, an ablation probe or catheter, an injection or fluid delivery device, a biopsy needle, an extraction tool, or the like may be accommodated to perform diagnosis and/or a therapeutic procedure.

Further, various brain disease-related drugs may be injected using the drug injection device 50. For example, the above-mentioned drugs may include dementia-related chemicals such as amyloid hypothesis (substance that inhibits β-amyloid protein production), Aβ protein aggregation inhibitor, tau aggregation inhibitor, cholinease inhibitor, NMDA receptor or antagonist, cholinergic precursor, anti-oxidant, or diabetes treatment drugs; stem cells such as human umbilical cord blood cells, human umbilical cord blood-derived mesenchymal stem cells, neural stem cells, or bone marrow stem cells; drugs for treating psychiatric diseases such as Parkinson's, depression, or schizophrenia; brain tumor and stroke-related therapeutic drugs; and the like.

The navigation device 10 may include a navigation probe 11, a navigation handle 13, an irradiation part 15, a sensor part 17, and an MRI imager 19. The navigation probe 11 may be a tracer, a sensor, or the like, and may function to find the target point 7 by adjusting a trajectory outside the skull 3 of the patient P. The navigation handle 13 is connected to the navigation probe 11, and may be manually operated by an operator. The irradiation part 15 is positioned on the navigation handle 13, and may transmit a signal to the sensor part 17 at a predetermined distance to inform an operation position of the patient's skull. The sensor part 17 emits a high frequency, and detects the high frequency reflected back from an object. A first role of the navigation probe 11 is to find the position of the target point 7 that is a lesion detected by the emitted high-frequency infrared rays. The MRI imager 19 may display the target point 7 found by the navigation probe 11 by magnetic resonance imaging (MRI) data, that is, 3D modeled data, or the like on a screen in real time. The operator may check the position of the target point 7 that is the lesion through the data displayed on the MRI imager 19. Further, a second role of the navigation probe 11 is to select a trajectory from the target point 7 in fastening the drug injection device 50 using the data displayed on the MRI imager 19. That is, the stereotactic guidance device 100 fastened to the skull 3 may select an accurate position by adjusting an angle from a central axis CL through direction change so as to be closest to the target point 7.

In this case, the MRI imager 19 is not limiting, and various medical imagers such as CT, MRA, fMRI, DTI, CTA, PET, and MEG may be used to obtain various information related to the patient's brain.

The stereotactic guidance device 100 may rotate the driving part 55 of the drug injection device 50 to find the target point 7 in the skull 3 of the patient P, and may be assembled and disassembled so that the guide tube unit 70 is mounted inside the driving part 55. Here, the stereotactic guidance device 100 may include a guide handle 110 and a probe accommodating part 120.

The guide handle 110 is provided inside the driving part 55, and is configured to accommodate the guide tube unit 70, guide the guide tube unit 70 to be mounted inside the driving part 55, and adjust the guide tube unit 70 to be positioned toward the target point 7. Further, the guide handle 110 may rotate and fix the driving part 55 toward the target point 7, so that the operator can easily handle the guide handle 110. In addition, the probe accommodating part 120 is mounted inside the guide handle 110, and the navigation probe 11 is inserted therein to guide the search for the target point 7.

The probe accommodating part 120, which is mounted in the guide handle 110 and accommodate the navigation probe 11 for finding the target point 7 and displaying its position on an MRI image, may prevent light dispersion with at least one side thereof being blocked. That is, in finding the target point 7 using the navigation probe 11, the probe accommodating part 120 can prevent decrease in precision and accuracy of detection due to shaking of the driving part 55 of the drug injection device 50 or light reflection inside the brain parenchyma 1.

FIG. 2 is an enlarged view of FIG. 1, which shows a state where the stereotactic guidance device 100 is positioned between the drug injection device 50 mounted on the patient's skull 3 and the navigation device 10 and performs the relay and guidance.

Referring to FIG. 2, the navigation probe 11 may be used to find the target point 7 through the main body 51 and the driving part 55 inserted into the skull 3 of the patient P. In this case, the guide handle 110 of the stereotactic guidance device 100 may be mounted inside the driving part 55. Further, the stereotactic guidance device 100 may include the guide handle 110 and the probe accommodating part 120.

The driving part 55 may include a first accommodating part 55a, a second accommodating part 55b, and a third accommodating part 55c. The first accommodating part 55a may have a large space at a central portion of the driving part 55, and the second accommodating part 55b may have a smaller area than that of the first accommodating part 55a. The third accommodating part 55c is positioned at a lower end portion of the driving part 55, and may have a narrower area, in which the guide tube 75 may be positioned in coupling of the guide tube unit 70.

The guide handle 110 may have a coupling hole 114 formed in a hollow shape so that at least one of the probe accommodating part 120, the navigation probe 11, a guide wire 150, and the guide tube unit 70 is inserted therein. The guide handle 110 may include an insertion part 117, a coupling part 115, a handling part 113, the coupling hole 114, and an insertion guide part 112. In a case where the guide handle 110 is mounted in the driving part 55, the insertion part 117 and the coupling part 115 of the guide handle 110 may be fixedly inserted in the first accommodating part 55a. On the other hand, since the handling part 113 of the guide handle 110 is exposed outside the driving part 55, the operator can easily handle the handling part 113 for the operation.

The probe accommodating part 120 may be formed with a probe insertion hole 121. The probe accommodating part 120 may further include a central axis aligning part 123. The probe insertion hole 121 may accommodate the navigation probe 11, and may be formed in a long tubular shape. At least one side of the central axis aligning part 123, which is inserted into the driving part 55, is flatly blocked, and is configured to find the nearest target point 7 by aligning the central axis CL without a direction error in a case where the driving part 55 rotates. Here, the central axis CL may be a straight line that passes through the inside of the driving part 55, that is, the center or the centripetal center of the third accommodating part 55$c$, which is orthogonal to a horizontal plane of the skull 3.

The central axis aligning part 123 may serve as a reference so that the navigation probe 11 is positioned to fit the central axis CL of the driving part 55. Specifically, one surface of the central axis aligning part 123 located inside the driving part 55 may be located at a position closest to the central portion of the skull 3. Further, the other surface thereof located in the probe insertion hole 121 is formed to be flat, and a center line or a center point of the driving part 55 orthogonal thereto may be imaged by the navigation probe 11. Accordingly, the central axis aligning part 123 may reduce a trajectory error of the navigation probe 11 as the driving part 55 rotates. However, the present invention is not limited thereto, and the probe accommodating part 120 may have a long tubular shape of which one side is blocked without the central axis aligning part 123.

A detailed description of other components forming the stereotactic guidance device 100 will be described below.

FIGS. 3A and 3B are a side view and a side sectional view showing a configuration of a guide handle 110 in the stereotactic guidance device shown in FIG. 2.

Referring to FIGS. 3A and 3B, the guide handle 110 may include the insertion part 117, the coupling part 115, the handling part 113, the coupling hole 114, and the insertion guide part 112.

The guide handle 110 is fastened inside the driving part 55, and may include the insertion part 117 to be inserted into the driving part 55, in which the coupling hole 114 is formed, and the coupling part 115 that is formed with a screw-thread.

The coupling hole 114 is a through hole formed at the center, in which at least one of the probe accommodating part 120, the navigation probe 11, the guide wire 150, and the guide tube unit 70 may be inserted.

The insertion part 117 which is inserted into the driving part 55 may be located in the first accommodating part 55$a$, and more specifically, may be located at the lower end portion of the first accommodating part 55$a$. Further, the insertion part 117 has a round end, and thus, can be easily inserted while preventing damage to the lower end portion of the first accommodating part 55$a$.

The coupling part 115 may be formed with a screw-thread, and a part of the first accommodating part 55$a$ may be formed with a screw-thread that is coupled and fastened with the coupling part 115. Accordingly, the coupling part 115 may prevent the guide handle 110 from being separated from the driving part 55. A part of the first accommodating part 55$a$ may be formed as a thread-shaped groove, and the insertion part 117 may be formed as a thread-shaped protrusion engaged with the groove. However, the present invention is not limited thereto, and the coupling part 115 and the first accommodating part 55$a$ may be formed with a thread-shaped protrusion and a thread-shaped groove to be fastened with each other.

The handling part 113 which is extended from the coupling part 115 is tapered so that the outer diameter is expanded toward its end to facilitate handling of the operator. Further, the handling part 113 may be exposed outside the driving part 55 for the handling of the operator, and may have a thickness greater than that of the coupling part 115.

The insertion guide part 112 that is provided at the end portion of the coupling hole inside the handling part 113 may be rounded to guide the insertion of a tube connecting part 130 in the direction of the coupling hole 114. In addition, the insertion guide part 112 which is connected to the coupling hole 114 is located at an external inlet portion of the guide handle 110, and may guide smooth insertion of the probe accommodating part 120.

Referring to FIGS. 3A and 3B, the handling part 113 may satisfy at least one of the following Expressions 1 and 2.

$$1 < D_{1a}/D_{1c} \leq 3 \qquad \text{[Expression 1]}$$

$$1 < L_1/L_{1a} \leq 6 \qquad \text{[Expression 2]}$$

Here, $D_{1a}$ represents an outer diameter of the handling part 113, $D_{1c}$ represents an inner diameter of the handling part 113, $L_1$ represents a total length of the guide handle 110, and $L_{1a}$ is a length of the section of the handling part 113.

In a case where $D_{1a}/D_{1c}$ is smaller than 1, since the degree of concentricity may be damaged due to an external force, the reliability of accurate targeting may be significantly reduced. Further, in a case where $D_{1a}/D_{1c}$ is greater than 3, since the size of the handling part 113 becomes excessively large, it may be difficult to secure a field of vision of the operator. Accordingly, in a case where Expression 1 is satisfied, the guide handle 110 can have an appropriate thickness, and thus, it is possible to guide the guide tube 75 or the navigation probe 11 to pass therethrough without damaging the inside thereof.

On the other hand, in a case where $L_1/L_{1a}$ is smaller than 1, it may be difficult to be coupled to the inside of the driving part 55. Further, in a case where $L_1/L_{1a}$ is greater than 6, since the length of the handling part 113 becomes excessively short, it may be difficult for the operator to perform the handling after fastening. Accordingly, in a case where the range of Expression 2 is satisfied, the ratio of the total length to the section of the handling part 113 becomes appropriate, and thus, it is possible to effectively provide the handling function.

The insertion part 117 may satisfy at least one of the following Expressions 3 and 4.

$$1 < D_{1c}/D_{1b} \leq 3 \qquad \text{[Expression 3]}$$

$$2.5 < L_1/L_{1b} \leq 9.6 \qquad \text{[Expression 4]}$$

Here, $D_{1b}$ represents an outer diameter of the insertion part 117, $D_{1c}$ represents an inner diameter of the insertion part 117, $L_1$ represents the total length of the guide handle 110, and Lib represents a length of the section of the insertion part 117 a body part 191.

In a case where $D_{1c}/D_{1b}$ is smaller than 1, since an outer thickness of the insertion part 117 becomes excessively thin, the insertion part 117 may be torn and damaged in a case where the guide wire 150 and the navigation device 10 are inserted. Further, in a case where $D_{1c}/D_{1b}$ is greater than 3, since the thickness of the insertion part 117 becomes excessively thick, the insertion of the guide tube 75 may not be possible. Accordingly, in a case where the range of Expression 3 is satisfied, the insertion part 117 can have an appropriate thickness, and thus, it is possible to guide the guide tube 75 to pass therethrough without damaging the inside thereof.

On the other hand, in a case where $L_1/L_{1b}$ is smaller than 2.5, since the height of the insertion part 117 becomes excessively small, the insertion part 117 may not touch the lower end portion of the driving part 55, so that the coupling part 115 is excessively fastened, which results in a risk that, when the guide handle 110 is removed, the driving part 55 may rotate together to change its position. Further, in a case where $L_1/L_{1b}$ is greater than 9.6, since a fastening space of the coupling part 115 becomes excessively small, the guide handle 110 may be easily separated. Accordingly, in a case where the range of Expression 4 is satisfied, the ratio of the length of the guide handle 110 to the section of a body part 191 may have an appropriate length for coupling with the driving part 55.

FIG. 4 shows a side sectional view showing a configuration of a probe accommodating part 120 in the stereotactic guidance device shown in FIG. 2, and a side view showing a central axis aligning part 123.

Referring to FIG. 4, the probe accommodating part 120 and the central axis aligning part 123 may satisfy at least one of the following Expressions 5 and 6.

$$7.5 \leq L_2/L_{2a} \leq 26 \qquad \text{[Expression 5]}$$

Here, $L_{2a}$ represents a length of the side of the central axis aligning part 123, and $L_2$ represents an entire length of the probe accommodating part 120.

In a case where $L_2/L_{2a}$ is smaller than 7.5, since the length of the probe accommodating part 120 fastened to the central axis aligning part 123 becomes excessively short, even if the navigation probe 11 is accommodated, there is a concern that the connecting portion may be separated, and in a case where $L_2/L_{2a}$ is greater than 26, since the length of the probe accommodating part 120 becomes excessively long, the probe accommodating part 120 may reach the navigation handle 13, to thereby make it difficult to handle the navigation device 10. Accordingly, in a case where the range of Expression 5 is satisfied, the probe accommodating part 120 and the central axis aligning part 123 can have such an appropriate length as to be inserted into the driving part 55 while accommodating the navigation probe 11 to align the central axis CL to find the target point.

$$1 < D_2/D_3 \leq 2.8 \qquad \text{[Expression 5]}$$

Here, $D_2$ represents an outer diameter of an upper end portion of the central axis aligning part, and $D_3$ represents an outer diameter of a lower end portion of the central axis aligning part.

In a case where $D_2/D_3$ is smaller than 1, since a difference between the outer diameters of the upper end portion and the lower end portion of the central axis aligning part 123 is not enough, the central axis aligning part 123 may be clogged when inserted into the probe accommodating part 120, and in a case where $D_2/D_3$ is greater than 2.8, since the outer diameter of the lower end portion of the central axis aligning part 123 becomes excessively small, the central axis aligning part 123 may be easily separated from the navigation probe 11, which causes a difficulty in fastening. Accordingly, in a case where the range of Expression 6 is satisfied, the fastening with the navigation probe 11 can be stably performed to prevent separation therefrom.

On the other hand, the end portion of the navigation probe 11 may contact the center of the lower end portion of the central axis aligning part 123, to thereby make it possible to measure a trajectory closest to the target point 7. In a case where the diameter of the probe insertion hole 121 is larger than the outer diameter of the navigation probe 11, the error of the trajectory may increase. That is, the trajectory found by the navigation probe 11 may be different from the trajectory at the time when the guide tube 75 is finally inserted in the driving part 55. Accordingly, the lower end portion of the central axis aligning part 123 may be positioned in the first accommodating part 55a of the driving part 55 and may be formed to be flat, so that the navigation probe 11 can find the trajectory for the target point 7 at a point that matches the central axis CL on the lower end portion thereof, and can reduce, even in a case where the driving part 55 is moved due to rotation, the error by precisely and accurately finding the moved trajectory.

FIGS. 5A to 5E are a perspective view showing states where the stereotactic guidance device according to the embodiment of the present invention is mounted.

More specifically, FIGS. 5A to 5E show states where the stereotactic guidance device 100 rotates the driving part 55 and is detachably provided so that the guide tube unit 70 is mounted inside the driving part 55.

Referring to FIGS. 5A to 5E, the stereotactic guidance device 100 according to the embodiment of the present invention may include the guide handle 110, the tube connecting part 130, and the guide wire 150. The main body 51 may be mounted on the skull 3 and the scalp 5 of the patient P, and may be formed with a through hole at the center thereof, in which the driving part 55 may be inserted. The driving part 55 may have an accommodating space at a central portion thereof.

The guide tube unit 70 may have a drug injection hole 77 through which a drug is injected at a central portion thereof. In addition, the guide tube unit 70 may include a first settling part 71, a second settling part 73, and a guide tube 75. A portion of the drug injection hole 77, which is positioned at the first settling part 71, is formed to be round, to thereby facilitate a drug syringe to enter the guide tube 75. The guide tube 75 may be formed in a long tubular shape so that an injector and a catheter for injecting a drug are inserted therein. Further, the guide tube 75 may accommodate the guide wire 150 for performing guidance so that the rotation direction of the trajectory can be changed.

The guide handle 110 may be inserted in the driving part 55. Then, the tube connecting part 130 may be mounted on or inserted in an upper end portion of the guide handle 110, and may be formed by assembly of at least one pair of members. That is, one end portion of the tube connecting part 130 may be inserted into the guide handle 110, and the other end portion thereof may be mounted on the upper end portion of the guide handle 110.

The tube connecting part 130 may be formed with a guide hole 137 at the central portion thereof, in which at least one of the guide wire 150 and the guide tube 75 is inserted and directed to the target point 7, and may serve as a double guide together with the guide handle 110. The tube connecting part 130 may include a first connecting part 131 and a second connecting part 135. The first connecting part 131 may be mounted on the guide handle 110 and may be in contact with the first settling part 71 of the guide tube unit 70. The second connecting part 135 is extended from the first connecting part 131, has a smaller diameter, and is inserted into the guide handle 110. An inlet portion of the guide hole 137 may be formed to be tapered like a funnel so that the guide tube 75 can be smoothly inserted into the center thereof in any direction.

The guide wire 150 may be inserted into the tube connecting part 130 together with the guide tube unit 70. That is, the guide wire 150 may guide the guide tube unit 70 to be stably inserted inside the driving part 55. The guide wire 150 may be formed in the shape of a long and rigid rod, and may be provided in the guide handle 110 and the guide tube unit 70. Further, the guide wire 150 may perform direction guidance and adjustment in a state of being positioned at the target point 7 while accommodating the guide tube 75 therein. The guide wire 150 is not limited to the rod shape, and may be made of a biocompatible material having strength and elasticity, and a property of memorizing an original shape and returning to the original shape, for example, shape memory alloy, titanium and titanium alloy, stainless steel, or the like.

As shown in FIG. 5C, in a case where the tube connecting part 130 comes into contact with the first settling part 71, the guide wire 150 may be inserted in the direction of the target point 7. The driving part 55 may be rotated with respect to the target point 7 before the guide wire 150 is inserted. Further, the guide tube unit 70, the tube connecting part 130, and the guide handle 110 provided in the driving part 55 may also be positioned in the same direction. After the direction of the guide wire 150 is determined as shown in FIG. 5D, the tube connecting part 130 may be separated from the guide handle 110 together with the guide tube unit 70, and the pair of members of the tube connecting part 130 that is formed by the first connecting part 131 and the second connecting part 135 may be separated from each other.

Referring to FIG. 5E, the guide tube unit 70 may be finally mounted in the driving part 55 by being inserted into the guide handle 110. The guide wire 150 may be separated and removed from the guide tube unit 70.

FIG. 6 is an exploded sectional view showing a state where a guide tube unit 70 in the drug injection device 50 mounted on the patient's skull 3 is guided using the stereotactic guidance device according to the embodiment of the present invention.

Referring to FIG. 6, the stereotactic guidance device 100 according to the embodiment of the present invention may guide the mounting of the guide tube unit 70 in the drug injection device 50. In a case where the direction perpendicular to the skull 3 of the patient P is defined as the central axis CL, the driving part 55 and the guide tube unit 70 may be located on the central axis CL. The stereotactic guidance device 100 may include the guide handle 110, the tube connecting part 130, the guide wire 150, the wire handling part 170, and a fastening part 190.

The driving part 55 is formed in a spherical shape, is formed with the first accommodating part 55*a*, the second accommodating part 55*b*, and the third accommodating part 55*c*, which are spaces for drug injection formed at the center thereof, and an upper portion thereof is open and a lower portion thereof is rotatable.

The first settling part 71 of the guide tube unit 70 is connected to the guide tube 75, has a diameter larger than that of the guide tube 75, and may be settled and supported in the driving part 55. The second settling part 73 is connected to the first settling part 71 to be located in the driving part 55, has a diameter smaller than that of the first settling part 71, and may connect the first settling part 71 and the guide tube 75.

The guide wire 150 is formed with a curved end to be inserted into the brain parenchyma 1, to thereby reduce damage when inserted into the brain parenchyma 1. In addition, the guide wire 150 may further include the wire handling part 170 for handling without shake during insertion into the target point 7 through the guide handle 110 and the procedure.

The wire handling part 170 is formed with a hole at a central portion thereof, into which the guide wire 150 is inserted, and may include a fixing part 173, a grip part 177, a mounting part 175, and a fastening accommodation part 179.

The fixing part 173 may be fixedly accommodated in the guide handle 110. The grip part 177 is connected to the fixing part 173, and may be formed with a gripping groove on at least one side thereof, which may be gripped in handling the guide wire 150. The mounting part 175 is connected to the grip part 177, and may be mounted on the guide handle 110. The fastening accommodation part 179 may be formed with a fastening groove on at least one side thereof to enable fixed coupling between the guide wire 150 and the wire handling part 170.

Further, the wire handling part 170 may further include the fastening part 190 to be fit-coupled in the fastening accommodation part 179. The fastening part 190 may include a head part 195, a body part 191, and a neck part 193. The head part 195 is formed with a concave and convex pattern on the outside thereof, which can prevent slipping in rotational handling of the fastening part 190. The body part 191 is fastened to the fastening accommodation part 179, and may provide the fixed coupling between the guide wire 150 and the wire handling part 170. The neck part 193 is positioned between the head part 195 and the body part 191, and may provide height adjustment to facilitate fastening and separation of the head part 195 and the body part 191.

On the other hand, the tube connecting part 130 is temporarily mounted on the upper portion of the guide handle 110 coupled to the driving part 55, and may be removed by separation of the pair of members thereof when the tube connecting part 130 comes into contact with the guide tube unit 70.

Figure 7:
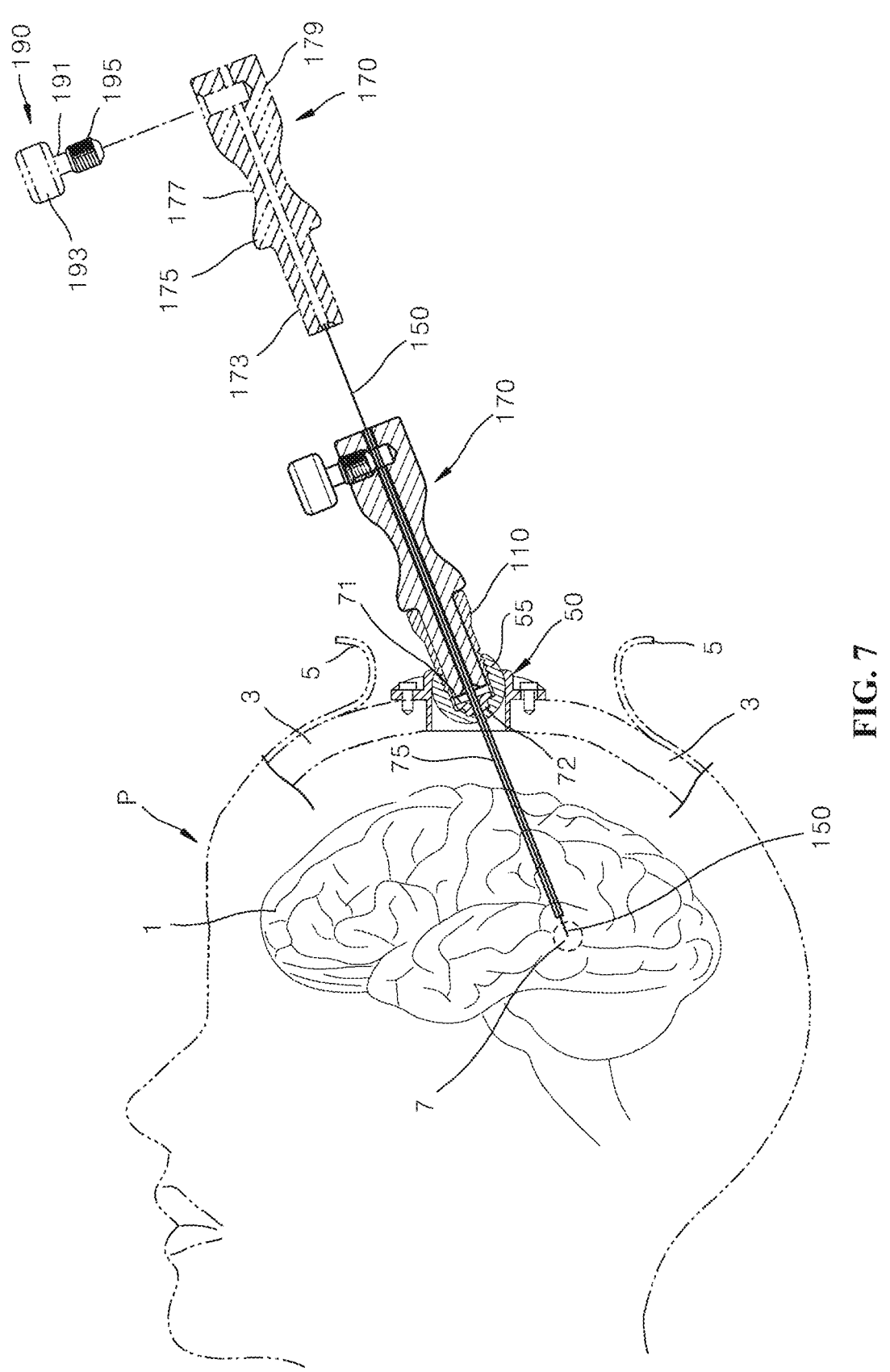
FIG. 7 is a view showing a state where the stereotactic guidance device according to the embodiment of the present invention guides the guide tube positioned on the central axis to change its direction from the central axis to be positioned at the target point.

FIG. 7 is a view showing a state where the stereotactic guidance device 100 according to the embodiment of the present invention guides the guide tube 75 located on the central axis CL to change its direction from the central axis CL to be positioned toward the position of the target point 7.

Referring to FIG. 7, the stereotactic guidance device 100 is coupled to the driving part 55 to change the direction of the guide tube 75 positioned on the central axis CL from the central axis CL toward the target point 7. Further, the stereotactic guidance device 100 may be separated and removed from the skull 3 after positioning the guide tube 75 as close to the target point 7 as possible.

Specifically, first, the stereotactic guidance device 100 may be temporarily coupled to the driving part 55.

Referring to FIGS. 2 and 7, the guide handle 110 may be mounted so that the coupling part 115 is coupled to the screw-threaded portion of the first accommodating part 55*a*. The guide tube unit 70 may be inserted inside the guide handle 110. In a case where the first accommodating part 55*a* of the driving part 55 is coupled to the guide tube unit 70, the first settling part 71 may be mounted at a lower end portion of the first accommodating part 55*a*. Further, the second settling part 72 may be settled on the second accommodating part 55*b*. The guide tube 75 may be inserted into third accommodating part 55*c* and may be fixedly accommodated therein. After the fastening part 190 is mounted on the wire handling part 170, the operator may hold the grip part 177 and may insert the guide wire 150 into the guide tube 75. The operator rotates the driving part 55 and the guide handle 110 fastened therein using the guide wire 150 coupled with the wire handling part 170 to be positioned toward the target point 7. Here, an optimal rotational angle may be within a maximum of 120° with reference to the horizontal plane of the skull 3.

Accordingly, the guide tube unit 70 may be inserted along the guide direction of the guide wire 150 inside the driving part 55 which is rotated toward the target point 7 and completes the positioning. Here, the guide wire 150 may precisely and accurately find the target point 7, and then, may guide the end portion of the guide tube 75 to be positioned close to the target point 7.

On the other hand, the stereotactic guidance device 100 may be made of at least one of titanium, stainless steel, and polyether ether ketone, which are biocompatible materials. However, the present invention is not limited thereto, and other various material having human insertion stability may be used.

Referring to FIGS. 1 to 7, a method of mounting and operating the stereotactic guidance device 100 will be described in detail as follows.

<Mounting and Operating Method>

A pre-operative preparation step is performed for finding a position of the target point 7 and marking the position on the skull 3 on coordinates using the navigation device 10 and MRI imaging (S10).

The pre-operative preparation step (S10) may include a step of inputting the position using the navigation probe 11 and transmitting images and photos using an MRI machine (S11).

Further, the pre-operative preparation step (S10) may include a step of finding the position of the target point 7 in the brain of the patient P on the basis of the images or photos obtained by MRI, and marking a plurality of reference sections on the scalp 5, that is, the subcutaneous layer (S13).

The type of the navigation probe 11 may be classified into a measurement probe and a verification probe. After checking a path using the verification probe before incision, the marking may be performed on the scalp 5 of the patient P. The pre-operative preparation step (S10) may include a step of incising the marked scalp 5 of the patient P in the shape of 'L', ']', 'S', or the like, for example (S15).

The pre-operative preparation step (S10) may include, after the incision, a step of spreading the incised site to secure a space for perforation, and tying the incised subcutaneous layer with a thread for treatment to fix the site so as not to be spread during the treatment (S17).

Here, the fixing and spreading may be performed using forceps or the like. Further, the pre-operative preparation step (S10) may include a step of inhaling foreign substances, blood, etc. using a suction catheter together with physiological saline as necessary in order to secure sight and visibility during the treatment (S17a).

The pre-operative preparation step (S10) may include a step of removing bone debris or residues with tweezers after making a bur hole in the skull 3 that is exposed due to the incision (S19).

Then, a step of implanting the drug injection device 50 in the perforated site (bur hole) of the skull 3 may be performed (S20). First, a step of implanting the main body 51 of the drug injection device 50 in the skull 3 may be performed (S21).

A step of fixedly fastening the main body 51 to the skull 3, inserting the driving part 55 therein, and performing fixing so that the driving part 55 can move using at least two bolts S in the hole of the main body 51 may be performed (S23).

A step of mounting the guide handle 110 in the driving part 55 may be performed (S25).

A step of mounting the probe accommodating part 120 to which the central axis aligning part 123 is assembled inside the guide handle 110, inserting the navigation probe 11 therein, and performing adjustment for finding the target point 7 while performing direction change may be performed (S27).

After the target point 7 is set, a step of separating and removing the navigation probe 11 and the probe accommodating part 120 from the guide handle 110 may be performed (S29).

A step of preparing the guide tube unit including the guide tube 75 integrated with the first and second settling parts 71 and 73 may be performed (S30).

Specifically, a step of fastening the wire handling part 170 and the fastening part 190 to the guide wire 150 as one set for position adjustment may be performed (S31).

Here, in a case where the wire handling part 170 reaches the portion in contact with the first settling part 71, a step of fixedly fastening the fastening part 190 to the fastening accommodating part 179 of the wire handling part 170 may be performed (S33).

A step of mounting the pair of detachable members of the tube connecting parts 130 at the upper end portion of the guide handle 110 and assembling the position adjustment set and the guide tube set may be performed (S40). The assembling step is as follows.

The guide wire 150 is inserted into the tube connecting part 130. The guide wire 150 may be inserted until the detachable tube connecting part 130 and the tube fixing part 173 come into contact with each other (S41).

The guide wire 150 is inserted until it reaches the end portion of the guide tube 75, and the fastening part 190 is fastened to the wire handling part 170 (S43).

The driving part 55 and the guide handle 110 fastened therein are rotated by a predetermined angle using the guide wire 150 mounted in the wire handling part 170 to be positioned toward the target point 7 (S50).

The wire handling part 170 may be adjusted so as to be in close toward the target point 7 in the brain parenchyma 1 (S51).

On the other hand, the rotation toward the target point 7 in the brain parenchyma 1 may be performed within a maximum angle of 60°, which may be not only performed by the method of positioning the guide tube 75 using the guide handle 110, but may also be performed by any method for rotating the driving part 55 into which only the guide tube 140 to be positioned toward the target point 7 (S53).

The guide tube unit 70 may be inserted along the guiding direction of the guide wire 150 inside the driving part 55 after the positioning is completed (S55).

The tube connecting part 130 may be separated and removed, and then, the first and second settling parts 71 and 73 may be pushed to be positioned at the lower end portions of the first to third accommodating parts 51a, 51b, and 51c of the driving part 55 (S57).

In a case where the guide tube 75 is located close to the target point 7, the position adjustment set may be separated and removed from the guide handle 110, and the guide handle 110 may also be separated and removed from the driving part 55 (S59).

A step of inserting a sealing member into the driving part 55 may be performed (S60).

A driving part cover (not shown) may be fastened using a dedicated driver for the procedure (S70).

The drug injection device 50 may be fixed on the skull 3 of the patient P by fastening the bolt S loosely located at the upper portion of the main body 51 once again (S80).

After the initial implantation of the drug injection device 50 is completed, a position indicating part of the driving part cover (not shown) may be visually identified to find the position (S90).

An injection needle containing a therapeutic agent may be sequentially inserted along a movable lid part, the first accommodating part 51a of the driving part 55, the sealing member, the drug injection hole 77 and the guide tube 75 of the guide tube unit 70 to reach the target point 7, to thereby repeatedly administer the therapeutic agent over a long period of time (S100).

FIGS. 8A to 8C are a side view, a plan view, and a side sectional view showing a configuration of the tube connecting part 130 in the stereotactic guidance device shown in FIGS. 5A to 5D and FIG. 6.

The tube connecting part 130 is connected to the guide handle 110 to insert and mount the guide tube unit 70 inside the guide handle 110, and includes at least one pair of members, which provides easy assembly and disassembly. Further, the tube connecting part 130 may guide the guide tube unit 70 to be inserted and settled inside the driving part 55 through the guide handle 110. Accordingly, the tube connecting part 130 may provide a double guidance together with the guide handle 110, to thereby guide at least one of the guide wire 150 and the guide tube 75 to go toward the target point 7 without going in a wrong direction.

The first connecting part 131 and the second connecting part 135 may satisfy at least one of Expressions 7 and 8 below.

$$1 < D_5/D_6 \leq 3 \qquad \text{[Expression 7]}$$

$$1 \leq L_4/L_3 \leq 3 \qquad \text{[Expression 8]}$$

Here, $D_5$ represents an outer diameter of the first connecting part 131, $D_6$ represents an outer diameter of the second connecting part 135, $L_3$ represents a height of the first connecting part 131, and $L_4$ represents a height of the second connecting part 135.

In a case where $D_5/D_6$ is smaller than 1, since the outer diameter of the second connecting part 135 may be larger than that of the first connecting part 131, the insertion and mounting in the guide handle 110 may be difficult, and in a case where $D_5/D_6$ is greater than 3, since a gap becomes excessively large when coupled with the inside of the guide handle 110, separation of the tube connecting part 130 may occur, or the insertion of the guide tube 75 may be difficult due to the large gap, which results in failure in the guide function. Accordingly, in a case where the range of Expression 7 is satisfied, the outer diameters and thicknesses of the first connecting part 131 and the second connecting part 135 can become appropriate to secure balance therebetween, and thus, the tube connecting part 130 can be stably coupled to the upper portion of the guide handle 110 without separation.

On the other hand, in a case where $L_4/L_3$ is smaller than 1, since the thickness of the first connecting part 131 is greater than that of the second connecting part 135, it is difficult to fix the tube connecting part 130 when inserted into the guide handle 110, which may cause easy separation. Further, in a case where $L_4/L_3$ is greater than 3, since the thickness of the first connecting part 131 may be smaller than that of the second connecting part 135, the tube connecting part 130 may be easily separated from the guide handle 110 when inserted therein. Accordingly, in a case where the condition range of Expression 8 is satisfied, the tube connecting part 130 can be stably inserted and mounted in the guide handle 110, to thereby stably guide the insertion of the guide tube unit 70, and easily perform separation and removal after the guidance.

FIG. 9 is a side view showing a configuration of the guide wire 150 in the stereotactic guidance device shown in FIGS. 5A to 5D and FIG. 6.

The guide wire 150 may have a curved end portion to satisfy at least one of the following Expressions 9 and 10.

$$0.5 \leq R_1 \leq 0.9[mm] \qquad \text{[Expression 9]}$$

$$55 \leq L_5/L_4 \leq 204 \qquad \text{[Expression 10]}$$

Here, $R_1$ represents a diameter of the end curve of the guide wire 150, $L_4$ represents an outer diameter of the guide wire 150, and $L_5$ represents a total length of the guide wire 150.

In a case where $R_1$ is smaller than 0.5, since the end portion of the guide wire 150 is almost straight, there is a concern that the brain parenchyma 1 may be damaged, and in a case where $R_1$ is greater than 0.9, since it does not fit the outer diameter of the guide wire 150, it may be difficult to form a rounded end. Accordingly, in a case where the range of Expression 9 is satisfied, since the leading end portion of the guide wire 150 inserted into the brain parenchyma 1 has a rounded or "U"-shaped end, it is possible to minimize tissue damage of the brain parenchyma 1 at the time of insertion of the guide tube 75 or the injection needle.

On the other hand, in a case where $L_5/L_4$ is smaller than 55, since the outer diameter of the guide wire 150 is excessively large, it may be difficult to be inserted into the inner diameter of the guide tube 75, and in a case where $L_5/L_4$ is greater than 204, since the thickness of the guide wire 150 is excessively thin, even in the case of being inserted into the inner diameter of the guide tube, it may be difficult to provide an appropriate guide function. Accordingly, in a case where the range of Expression 10 is satisfied, since the ratio of the thickness and the length of the guide wire 150 becomes appropriate, it is possible to guide position adjustment of the guide tube 75 while precisely adjusting the position of the target point 7 when inserted into the inner diameter of the guide tube 75.

FIG. 10 is a side view showing a configuration of a wire handling part 170 coupled to the guide wire 150 shown in FIG. 9.

Referring to FIG. 10, the fixing part 173, the grip part 177, the mounting part 175, and the fastening accommodation part 179 may satisfy at least one of the following Expression 11, Expression 12, and Expression 13, respectively.

$$1 < D_7/D_6 \leq 4 \qquad \text{[Expression 11]}$$

$$5 \leq R_2 \leq 15[mm] \qquad \text{[Expression 12]}$$

$$0.3 \leq (L_{6a} + L_{6b})/L_6 < 1 \qquad \text{[Expression 13]}$$

Here, $D_6$ represents an outer diameter of the fixing part 173, $D_7$ represents an outer diameter of the mounting part 175, and $R_2$ represents a diameter of a curve of the grip part 177. Further, $L_6$ represents a total length of the wire handling part 170, $L_{6a}$ represents a length of the section of the fastening accommodation part 179, and $L_6b$ represents a length of the section of the fixing part 173.

In a case where $D_7/D_6$ is smaller than 1, since a difference between the thicknesses of the fixing part 173 and the mounting part 175 is not enough, there is a concern that the wire handling part 170 may not be mounted on the guide handle 110 or the tube connecting part 130 during insertion, and in a case where $D_7/D_6$ is greater than 4, since the mounting part 175 has an excessively large thickness, when mounted on the guide handle 110 or the tube connecting part 130, the guide handle 110 or the tube connecting part 130 may be damaged. Accordingly, in a case where the condition range of Expression 11 is satisfied, the fixing part 173 and the mounting part 175 having an appropriate ratio to be inserted and mounted to the guide handle 110 or the tube connecting part 130 can be provided.

On the other hand, in a case where $R_2$ is smaller than 5 or greater than 15, it may be difficult for the operator to perform the operation while holding the grip part 177. Accordingly, in a case where the condition range of Expression 12 is satisfied, the operator can easily perform the operation while stably holding the grip part 177, to thereby precisely and accurately adjust the guide wire 150.

Further, in a case where $(L_{6a}+L_{6b})/L_6$ is greater than 1, since the wire handling part 170 has a structure in which the grip part 177 is not provided, it may be difficult for the operator to handle the guide wire 150. Further, in a case where $(L_{6a}+L_{6b})/L_6$ is smaller than 0.3, since only one of the fixing part 173 and the fastening accommodation part 179 of the wire handling part 170 may be provided, it is not possible to insert the wire handling part 170 into the guide handle 110, or it may be difficult to mount the fastening part 190 for fastening the guide wire 150. Even in a case where the fixing part 173 and the fastening accommodation part 179 are present, since the distance therebetween becomes excessively large, it may be difficult to handle the guide wire 150. Accordingly, in a case where the condition range of Expression 13 is satisfied, since the wire handling part 170 may have an appropriate configuration of the fixing part 173, the grip part 177, and the fastening accommodation part 179, the operator can easily handle the guide wire 150, can stably control the wire handling part 170 by the operator's hand during the procedure, and can prevent separation from the guide wire 150 by fastening the wire handling part 170 with the fastening part 190.

FIG. 11 is a side view showing a configuration of a fastening part 190 fastened to the wire handling part 170 shown in FIG. 9.

Referring to FIG. 11, the fastening part 190 may satisfy at least one of the following Expressions 14 and 15.

$$0.5 \leq (L_8+L_9)/L_7 < 1 \qquad \text{[Expression 13]}$$

$$1 < D_8/D_9 \leq 5 \qquad \text{[Expression 15]}$$

Here, $L_7$ represents a total length of the fastening part 190, $L_8$ represents a length of the head part 195, and $L_9$ represents a length of the body part 191. Further, $D_8$ represents a diameter of the head part 195, and $D_9$ represents a diameter of the neck part 193.

In a case where the condition of Expression 14 is out of the range, since it results in a structure of the fastening part 190 in which the neck part 193 is not provided, it takes a long time to insert and fasten the body part 191 in the wire handling part 170, and it may be difficult to easily separate and remove the body part 191 after fastening. Accordingly, in a case where the condition range of Expression 14 is satisfied, it is possible to provide the neck part 193 having a length of about 0.5 mm to 5 mm in the fastening part 190. Since the head part 195 can move up and down in a state where the neck part 193 is provided between the head part 195 and the body part 191, it is possible to easily fasten and separate the fastening part 190 with respect to the wire handling part 170. Further, the fastening part 190 including the neck part 193 can save time necessary for fastening to the wire handling part 170.

On the other hand, in a case where $D_8/D_9$ is smaller than 1, since the diameter of the neck part 193 becomes excessively large, it may be difficult to secure the fastening function of the head part 195. Further, in a case where $D_8/D_9$ is greater than 5, since the diameter of the neck part 193 becomes excessively small, it may be difficult to handle the head part 195 in fastening. Accordingly, in a case where the range of Expression 15 is satisfied, the fastening part 190 can be stably fastened to the wire handling part 170 without separation therefrom.

FIG. 12 is a perspective view showing a configuration of a tube connecting part in a stereotactic guidance device according to another embodiment of the present invention.

Referring to FIG. 12, a tube connecting part 200 of another embodiment according to the present invention is different from the tube connecting part 130 of the above-described embodiment in that the tube connecting part 200 is not mounted on the guide handle 110. The tube connecting part 200 is formed in a long tubular shape, and is configured as a pair of members that is detachably coupled to each other. Further, the tube connecting part 200 is mounted on the guide handle 110, and the guide tube unit 70 may be inserted therein. In a case where the first settling part 71 of the guide tube unit 70 comes into contact with an upper portion of the tube connecting part 200, the tube connecting part 200 may be pulled out from the guide handle 110. Then, the tube connecting part 200 may be separated and removed from the guide tube unit 70. Accordingly, the tube connecting part 200 can accurately and precisely position the guide tube 75 toward the target point 7. An inlet portion of the tube connecting part 200 may be formed to be rounded like a funnel, so that the guide tube 75 can be guided to the center thereof even in a case where the guide tube 75 is inserted in an arbitrary direction.

The above-described embodiments are merely exemplary, and various modifications and equivalent other embodiments are possible by those skilled in the art to which the present invention belongs. Accordingly, the true technical protection scope of the present invention should be determined by the technical idea of the invention described in claims.

What is claimed is:

1. A stereotactic guidance device that rotates a driving part of a drug injection device in order to find a target point in a patient's skull and is detachably provided so that a guide tube unit can be provided in the driving part, comprising:

a guide handle that is coupled inside the driving part, and is configured to accommodate the guide tube unit, adjust the guide tube unit to be positioned toward the target point, and guide the guide tube unit so that the guide tube unit is provided inside the driving part;

a probe accommodating part that is provided at the guide handle and accommodates a navigation probe that finds a trajectory for the target point;

a tube connecting part that is connected to the guide handle, is provided as at least a pair of members to be assembled and disassembled, has one end portion inserted into the guide handle and the other end portion mounted at an upper portion of the guide handle, and guides the guide tube unit so that the guide tube unit is inserted into and mounted in the driving part; and a guide wire that is provided in the guide handle and the guide tube unit, and guides and adjusts a direction toward the target point.

2. The stereotactic guidance device according to claim 1, wherein the guide handle has a coupling hole that is formed in a hollow shape so that at least one of the probe accommodating part, the navigation probe, the guide wire, and the guide tube unit is inserted therein, and includes:

an insertion part that is inserted in the driving part;

a coupling part that is extended from the insertion part and is coupled to the driving part;

a handling part that is formed to be tapered in the coupling part and is located outside the driving part to perform handling during a procedure; and an insertion guide part that is formed to be rounded inside the handling part, is located at an end portion of the coupling hole, and guides insertion of the tube connecting part in a direction of the coupling hole when the tube connecting part is inserted therein.

3. The stereotactic guidance device according to claim 1, wherein a probe insertion hole is formed inside the probe accommodating part, and the probe accommodating part includes a central axis aligning part that has at least one side that is inserted into the driving part and is flatly blocked, and is configured to find the nearest target point by aligning the central axis without a direction error when the driving part rotates.

4. The stereotactic guidance device according to claim 1, wherein the tube connecting part is formed with a guide hole at the central portion thereof, in which at least one of the guide wire and the guide tube is inserted and directed to the target point, and serves as a double guide together with the guide handle, and includes:

a first connecting part that is mounted on the guide handle; and a second connecting part that is extended from the first connecting part, has a smaller diameter, and is inserted into the guide handle.

5. The stereotactic guidance device according to claim 1, wherein the guide wire is formed in a round shape at a tip thereof capable of being inserted into brain parenchyma.

6. The stereotactic guidance device according to claim 1, further comprising:

a wire handling part is formed with a hole in which the guide wire is inserted at a central portion thereof.

7. The stereotactic guidance device according to claim 6, wherein the wire handling part includes:

a fixing part that is fixedly accommodated in the guide handle;

a grip part that is connected to the fixing part and is formed with a gripping groove to be gripped in handling the guide wire on at least one side thereof;

a mounting part that is connected to the grip part and is mounted on the guide handle; and a fastening accommodation part that is formed with a fastening groove on at least one side thereof to enable fixed coupling between the guide wire and the wire handling part.

8. The stereotactic guidance device according to claim 7, wherein the wire handling part further includes a fastening part that is provided to be fit-coupled in the fastening accommodation part, and the fastening part includes:

a head part having a concave and convex pattern formed on the outside thereof to prevent slipping in rotational handling of the fastening part;

a body part that is fastened to the fastening accommodation part, and provides the fixed coupling between the guide wire and the wire handling part; and a neck part that is positioned between the head part and the body part, and is configured to provide height adjustment to facilitate fastening and separation of the head part and the body part.

\* \* \* \* \*